(12) United States Patent
Feddes et al.

(10) Patent No.: US 8,937,481 B2
(45) Date of Patent: Jan. 20, 2015

(54) CAPACITIVE SENSING APPARATUS

(75) Inventors: Bastiaan Feddes, Eindhoven (NL);
Lena Gourmelon, Eindhoven (NL);
Mohammed Meftah, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 265 days.

(21) Appl. No.: 13/318,803

(22) PCT Filed: May 21, 2010

(86) PCT No.: PCT/IB2010/052270
§ 371 (c)(1),
(2), (4) Date: Nov. 4, 2011

(87) PCT Pub. No.: WO2010/136946
PCT Pub. Date: Dec. 2, 2010

(65) Prior Publication Data
US 2012/0056631 A1    Mar. 8, 2012

(30) Foreign Application Priority Data

May 29, 2009  (EP) .................................. 09161512

(51) Int. Cl.
| | |
|---|---|
| *G01R 27/26* | (2006.01) |
| *A61B 5/05* | (2006.01) |
| *A61B 5/0408* | (2006.01) |
| *A61B 5/0478* | (2006.01) |
| *A61B 5/0492* | (2006.01) |
| *A61B 5/00* | (2006.01) |

(52) U.S. Cl.
CPC ............. *A61B 5/0408* (2013.01); *A61B 5/0478* (2013.01); *A61B 5/0492* (2013.01); *A61B 5/7207* (2013.01)

USPC .......................... 324/686; 324/690; 600/424

(58) Field of Classification Search
CPC .. A61B 5/0408; A61B 5/7207; A61B 5/0492; A61B 5/0478
USPC .................................... 324/658–690; 600/424
See application file for complete search history.

(56) References Cited

U.S. PATENT DOCUMENTS

| | | | |
|---|---|---|---|
| 3,500,823 A | 3/1970 | Richardson et al. | |
| 4,082,086 A | 4/1978 | Page et al. | |
| 5,444,382 A | * 8/1995 | Mercer | ......................... 324/690 |
| 5,753,820 A | 5/1998 | Reed et al. | |
| 5,976,094 A | 11/1999 | Gozani | |

(Continued)

FOREIGN PATENT DOCUMENTS

| | | |
|---|---|---|
| JP | 2006320484 A | 11/2006 |
| WO | 03103174 A1 | 12/2003 |

*Primary Examiner* — Melissa Koval
*Assistant Examiner* — Farhana Hoque (57) ABSTRACT

The invention relates to a capacitive sensing apparatus for sensing an object, wherein the capacitive sensing apparatus comprises a capacitive sensor (2) for capacitively sensing the object (3) and an enclosure (4) for enclosing the capacitive sensor (2). The enclosure (4) comprises a contact side (6) for contacting the object (3) during sensing, wherein the enclosure (4) and the capacitive sensor (2) are adapted for sensing the object (3) by the capacitive sensor (2) through the contact side (6) of the enclosure (4). The enclosure (4) and the capacitive sensor (2) are separable from each other for using the capacitive sensor (2) as a reusable device and for using the enclosure (4) as a disposable device. This allows capacitively sensing an object with a new, uncontaminated enclosure (4) and a reused capacitive sensor (2) and, thus, under improved hygienic conditions.

17 Claims, 6 Drawing Sheets

(56) References Cited

U.S. PATENT DOCUMENTS

| | | |
|---|---|---|
| 6,117,086 A | 9/2000 | Shulze |
| 6,366,099 B1 * | 4/2002 | Reddi ............................ 324/678 |
| 6,461,037 B1 | 10/2002 | O'Leary |
| 6,972,575 B2 * | 12/2005 | Lambert et al. ............... 324/658 |
| 7,085,542 B2 * | 8/2006 | Dietrich et al. .............. 455/90.3 |
| 7,757,096 B2 | 7/2010 | Murata et al. |
| 7,835,553 B2 | 11/2010 | Miyasaka |
| 8,193,821 B2 | 6/2012 | Mueller et al. |
| 2003/0080757 A1 * | 5/2003 | Groover et al. ............... 324/662 |
| 2004/0019293 A1 | 1/2004 | Schweitzer et al. |
| 2004/0073104 A1 | 4/2004 | Brun del Re et al. |
| 2005/0248357 A1 * | 11/2005 | McQueeney et al. ......... 324/686 |
| 2009/0018410 A1 * | 1/2009 | Coene et al. ................... 600/301 |
| 2009/0318796 A1 * | 12/2009 | Datta et al. .................... 600/424 |

* cited by examiner

CAPACITIVE SENSING APPARATUS

FIELD OF THE INVENTION

The invention relates to a capacitive sensing apparatus for sensing an object and a capacitive sensing method for sensing an object.

BACKGROUND OF THE INVENTION

U.S. Pat. No. 3,500,823 discloses electrodes for electrocardiographic and bioelectric recording. These electrodes comprise an aluminum disc with an insulating coating. The insulating coating is applied through an anodizing process. The electrodes are placed directly on the unprepared skin of the patient for recording electrocardiographic and bioelectric signals.

However, up to now these electrodes are normally not used in the field of electrophysiological sensing, because they do not fulfill the requirements with respect to hygiene.

SUMMARY OF THE INVENTION

It is an object of the present invention to provide a capacitive sensing apparatus for sensing an object, wherein the sensing can be performed under improved hygienic conditions.

In an aspect of the present invention a capacitive sensing apparatus for sensing an object is presented, wherein the capacitive sensing apparatus comprises:

a capacitive sensor for capacitively sensing the object,
an enclosure for enclosing the capacitive sensor, wherein the enclosure comprises a contact side for contacting the object during sensing, wherein the enclosure and the capacitive sensor are adapted for sensing the object by the capacitive sensor through the contact side of the enclosure and wherein the enclosure and the capacitive sensor are separable from each other for using the capacitive sensor as a reusable device and for using the enclosure as a disposable device.

During sensing the object the contact side of the enclosure contacts the object, wherein the object is sensed through the contact side by the capacitive sensor. Since the capacitive sensor and the enclosure are separable from each other such that the capacitive sensor can be used as a reusable device and such that the enclosure can be used as a disposable device, for each sensing procedure an enclosure can be used, which is used for the first time and which is therefore not contaminated by a previous sensing procedure, whereas the generally more expensive capacitive sensor can be used for several sensing procedures. This allows capacitively sensing the object under improved hygienic conditions.

The capacitive sensing apparatus is preferentially adapted for capacitively sensing electrophysiological signals like ECG, EMG, EEG, EOG, EHG et cetera signals. The capacitive sensing apparatus is preferentially adapted for sensing an electrophysiological signal of a patient for monitoring the patient.

The capacitive sensor can be a device comprising all elements being required for capacitively sensing the object. However, the capacitive sensor can also only comprise a part of these elements, wherein further elements required for capacitively sensing the object are, for example, integrated in the enclosure such that the capacitive sensor and the enclosure cooperate for sensing the object.

The enclosure can be adapted to not completely enclose the capacitive sensor, in particular, the enclosure preferentially comprises the contact side and lateral surrounding elements like surrounding walls for surrounding the capacitive sensor for holding the capacitive sensor in place. In an embodiment, the enclosure can also be adapted to completely enclose the capacitive sensor.

The part of the contact side which is intended to contact the object is preferentially made of a biocompatible material.

It is further preferred that at least one of the capacitive sensor and the enclosure comprises a retaining element for retaining the capacitive sensor within the enclosure.

Preferentially, the retaining element is a notch element for clicking the capacitive sensor within the enclosure and for retaining the capacitive sensor within the enclosure in place. The retaining element can be adapted such that a "click" is heard and/or felt, if the capacitive sensor is introduced into the enclosure such that the capacitive sensor is retained within the enclosure. Thus, preferentially the retaining element can give, for example, a patient or a nurse feedback on whether the capacitive sensor is correctly retained within the enclosure by hearing a "click" and/or by feeling a "click", i.e. by feeling a pressure transmission on the skin.

It is further preferred that the enclosure comprises at least one surrounding element, which is arranged on the contact side and which is adapted to surround the capacitive sensor for holding the capacitive sensor in place.

It is further preferred that the at least one surrounding element is flexible for forming a clamping mechanism for holding the capacitive sensor in place.

The at least one surrounding element is preferentially at least a lateral element like at least one lateral wall for surrounding the capacitive sensor. The at least one surrounding element is adapted to conform to the shape of the capacitive sensor. If, for example, the capacitive sensor has a cylindrical outer shape, the at least one surrounding element is preferentially a ring element. A single surrounding element can completely surround a capacitive sensor or several surrounding elements can surround a capacitive sensor. If several surrounding elements surround a capacitive sensor, preferentially at least one gap is provided between two of these several surrounding elements. Thus, the surrounding elements can form a non-segmented holder or a segmented holder.

It is further preferred that at least one of the capacitive sensor and the enclosure comprises a release mechanism for releasing the capacitive sensor from the enclosure. The release mechanism allows for an easy removal of the capacitive sensor from the enclosure. For example, the release mechanism can be a spring release mechanism, wherein a spring forces the capacitive sensor out of the enclosure. Furthermore, the release mechanism can be integrated in the surrounding element, for example, by using an elastic or flexible surrounding element which can be pushed for detaching the capacitive sensor from the enclosure.

It is further preferred that the enclosure is adapted for enclosing several capacitive sensors.

Such an arrangement is beneficial, if, for example, a sensing of the object has to be performed at several positions, which are close to each other. For example, in electrophysiological sensing procedures several capacitive sensors might be needed, which have to be located close to each other, for instance, in bipolar or other configurations.

It is further preferred that the enclosure comprises a first at least one surrounding element for holding a first capacitive sensor in place and a second at least one surrounding element for holding a second capacitive sensor in place, wherein the first at least one surrounding element and the second at least one surrounding element are arranged on the same contact side.

This allows to easily integrate several capacitive sensors on a single contact side. Moreover, this arrangement allows to locate several capacitive sensors on the object by arranging only a single enclosure with the contact side on the object. Two, three or more capacitive sensors can be arranged on the same contact side and surrounded by corresponding surrounding elements.

It is further preferred that the capacitive sensor is formed of an array of capacitive sensing elements.

Also this allows to arrange several capacitive sensing elements on the object by simply arranging the enclosure on the object. Furthermore, this allows to sense the object at sensing positions which are close to each other.

It is further preferred that the enclosure comprises at least one surrounding element for surrounding the array of capacitive sensing elements.

It is preferred that a single surrounding element surrounds the array of capacitive sensing elements for holding the array of capacitive sensing elements. This allows an easy and fast connection of multiple capacitive sensing elements with the enclosure, wherein the object can be sensed capacitively at different points by simply attaching the single enclosure with the array of capacitive sensing elements on the object.

It is further preferred that at least one of the capacitive sensor and the enclosure is coded.

The capacitive sensor and/or the enclosure are preferentially coded by different colors, different shapes or different icons. If several capacitive sensors and/or several enclosures are present, by using the coding it can be ensured that a capacitive sensor and an enclosure, which belong together, are put together.

It is further preferred that the enclosure comprises a cap for closing the enclosure after the capacitive sensor has been introduced into the enclosure.

For example, if the enclosure comprises the contact side being, for example, a foil, and at least one surrounding element, the contact side and the at least one surrounding element define a container, wherein the cap can cover the remaining open side of the container, i.e. of the enclosure, preferentially automatically. The use of a cap for closing the enclosure can prevent contamination of the capacitive sensor located within the enclosure.

It is further preferred that the contact side of the enclosure comprises an attachment means for holding the enclosure at a constant position on the object.

The attachment means is, for example, an adhesive, in particular, a biocompatible adhesive, which is preferentially applied to the outer surface of the contact side of the enclosure. The attachment means can also be a strapping element being adapted such that the enclosure can be hold on the object such that the contact side of the enclosure contacts the object.

It is further preferred that the contact side is a foil.

The contact side is preferentially made of a thin material, preferentially of a material having a thickness in a sub-micrometer to sub-millimeter range. The thinner material the higher the capacitive coupling or the body resulting in a higher bio electric signal transfer.

The contact side can be made of an insulating material. Since the contact side can be made of an insulating material, in comparison to traditional sensing materials used for sensing electrophysiological signals a wider range of possible materials is available including insulating biocompatible materials, cheaper material, more comfortable materials et cetera.

The contact side can be made of an electrically conducting material. This is beneficial for the reduction of triboelectric charge which might damage the object or the capacitive sensing apparatus.

It is further preferred that the contact side comprises a high relative permittivity material.

A high permittivity material is a material having a relative permittivity larger than 10, preferentially larger than 30, further preferred larger than 100 and even further preferred larger than 500.

A contact side comprising a high relative permittivity material ensures a sufficient capacitive coupling between the electrode, in particular, the capacitive sensor, and the object to be sensed. The contact side preferentially comprises at least one of the following materials: AgCl (11.2), BaO (34), $BaTiO_3$ (80-3600, anisotropic), $BaZrO_3$ (43), $CaTiO_3$ (165), $Cd_2Nb_3O_7$ (500-580), $KH_3PO_4$ (46), $KNO_3$ (25), $KNbO_3$ (700), $KTaNbO_3$ (6000-34000), $NH_4HSO_4$ (165), $NaNbO_3$ (670), $Pb_3MgNb_2O_4$ (10000), $PbTiO_3$ (200), SbSI (2000), SnTe (1770), $SrTiO_3$ (382), $Ta_2O_5$ (30-65, anisotropic), $TiO_2$ (86-170, anisotropic), $WO_3$ (300), $ZrO_2$ (12.5). In the previous list of materials the numbers in brackets denote the relative permittivity of the respective material.

The contact side, in particular, the surface of the contact side facing the object during sensing, is preferentially non-toxic, in particular, is preferentially biocompatible. Thus, the contact side comprises preferentially at least one of the following materials: AgCl, BaO, $BaTiO_3$, $BaZrO_3$, $CaTiO_3$, $KH_3PO_4$, $Ta_2O_5$, $TiO_2$, $WO_3$ and $ZrO_2$. These materials are preferentially used as a solid insulating coating on the contact side of the enclosure.

It is further preferred that the capacitive sensor and the enclosure are adapted such that there is no air gap between the capacitive sensor and the enclosure towards the contact side.

Since a small air gap would strongly lower the capacitive coupling and since slight variations in an air gap even induce strong artifacts during use of the capacitive sensing apparatus, the quality of the capacitive sensing is improved if the capacitive sensor and the enclosure are adapted such that there is no air gap between the capacitive sensor and the enclosure towards the contact side, i.e. in the sensing direction.

Furthermore, preferentially the capacitive sensor apparatus, in particular, the contact side of the enclosure, is adapted such that an air gap is generally not present between the contact side and the object, in particular, the skin of the body, for further improving the quality of the capacitive sensing. Preferentially, in order to reduce the probability of an air gap between the object to be sensed and the contact side, the surface of the contact side facing the object during sensing is plane.

It is also further preferred that the contact side comprises a low relative permittivity material.

A low permittivity material is a material having a relative permittivity smaller than 10, preferentially smaller than 5 and further preferred smaller than 3.

If the appearance of air gaps is likely, a relative permittivity material as close as possible to air reduces motion artifacts. Therefore, also following materials can be preferred materials for the contact side: non-oxygen containing polymers like polytetrafluorethylene (2.1), polyethylene/polypropylene (2.3), polybutadiene (2.5), polystyrene (2.6), natural rubber (2.6), polycarbonate (2.9). Also silicon rubber (3) is a preferred material of the contact side, in particular, because of its good biocompatible nature. Also in this paragraph the numbers in brackets denote relative permittivity values.

Also nanostructured materials having a relative permittivity smaller than 2.0, further preferred smaller than 1.5, and even further preferred smaller than 1.2 can be used as material for the contact side. These materials can be useful to create a well controlled thickness with a low relative permittivity while maintaining a barrier between the re-useable capacitive sensor and the object, in particular, the skin, for hygienic purposes.

It is further preferred that the capacitive sensor comprises an electrode, electronics electrically connected to the electrode and an electrical shielding for shielding the electronics and preferentially the electrode, wherein the electronics and preferentially the electrode are located within the electrical shielding.

The electronics are preferentially adapted to reduce the impedance of the capacitive sensor in order to measure a larger signal, i.e. the electronics are preferentially adapted to make the signal low impedant. Since capacitive sensing is generally extremely high impedant, such an adaptation of the electronics leads to a reduced sensitivity to noise. Alternatively or in addition, the electronics can be adapted to amplify the signal, to perform some signal conditioning like filtering or to perform further functions like neutralization and/or bootstrapping.

Preferentially, the electrode, the electrical shielding and the electronics are formed as a single component which can be arranged within the enclosure. The electrode is preferentially an electrode plate. If the capacitive sensor comprises the electrode, the electronics and the electrical shielding, the capacitive sensing apparatus can easily be put together by putting the capacitive sensor in the enclosure. The capacitive sensor can also comprise more modules for further functions, for example, the capacitive sensor can comprise a wireless communication unit, a battery, a signal processing unit et cetera. The shielding can be a passive shielding or an active shielding.

It is further preferred that the electrical shielding is formed as a casing made of conducting material, wherein a side of the casing forms the electrode and wherein the electronics are arranged within the casing.

The casing is preferentially formed such that it corresponds to the shape of the enclosure. Preferentially, the casing has a cylindrical shape. However, the casing can also have another shape, for example, a rectangular shape.

It is preferred that the enclosure comprises an electrode, wherein the capacitive sensor comprises electronics, for example, for reducing the impedance of the capacitive sensor, and an electrical shielding for shielding the electronics and preferentially the electrode, wherein the enclosure and the capacitive sensor are adapted such that the electrode and the electronics are electrically connected, if the capacitive sensor is arranged within the enclosure.

It is preferred that the capacitive sensor is wired via the enclosure. For example, if multiple capacitive sensors are used in a single enclosure, the shared wires, for, for example, power supply, ground, reference, can be integrated into the enclosure in order to minimize the amount of wires going to the capacitive sensors.

In a further aspect of the present invention an enclosure for enclosing a capacitive sensor for forming a capacitive sensing apparatus for sensing an object is provided, wherein the enclosure comprises a contact side for contacting the object during sensing the object, wherein the enclosure is adapted for sensing the object by the capacitive sensor through the contact side of the enclosure and wherein the enclosure is separable from the capacitive sensor for using the enclosure as a disposable device.

In a further an aspect of the present invention a capacitive sensor for being enclosed by an enclosure for forming a capacitive sensing apparatus for sensing an object is provided, wherein the capacitive sensor is adapted for sensing the object through a contact side of the enclosure and wherein the capacitive sensor is separable from the enclosure for using the capacitive sensor as a reusable device.

In a further aspect of the present invention a capacitive sensing method for sensing an object is provided, wherein the object is capacitively sensed by a capacitive sensing apparatus comprising a capacitive sensor for capacitively sensing the object and an enclosure for enclosing the capacitive sensor, wherein the enclosure comprises a contact side for contacting the object during sensing, wherein the object is sensed through the contact side of the enclosure by the capacitive sensor.

It is preferred that before sensing the object the capacitive sensor is separatably enclosed within the enclosure and that after sensing the object the capacitive sensor is separated from the enclosure for using the capacitive sensor as a reusable device and for using the enclosure as a disposable device.

It shall be understood that a preferred embodiment of the invention can also be any combination of the dependent claims with the respective independent claim.

DETAILED DESCRIPTION OF EMBODIMENTS

Figure 1:
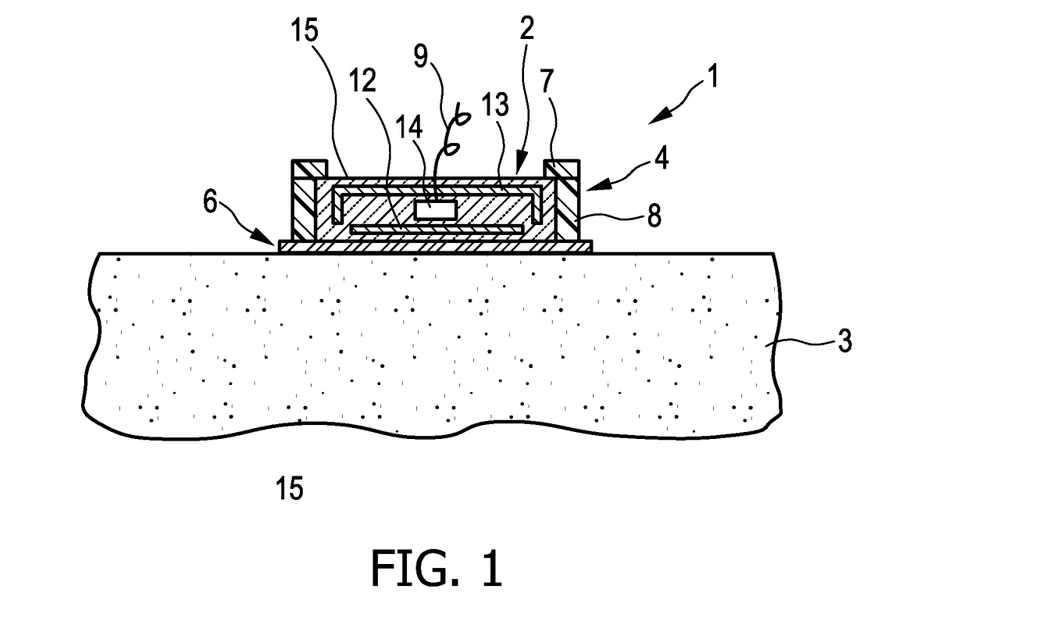
FIGS. 1 to 4 show schematically and exemplary different embodiments of a capacitive sensing apparatus.

FIG. 1 shows schematically and exemplarily an embodiment of a capacitive sensing apparatus 1 for sensing an object 3. The capacitive sensing apparatus 1 comprises a capacitive sensor 2 for capacitively sensing the object 3. The capacitive sensing apparatus 1 further comprises an enclosure 4 for enclosing the capacitive sensor 2, wherein the enclosure 4 comprises a contact side 6 for contacting the object 3 during sensing. The enclosure 4 and the capacitive sensor 2 are adapted for sensing the object 3 by the capacitive sensor 2 through the contact side 6 of the enclosure 4. The enclosure 4 and the capacitive sensor 2 are separable from each other for using the capacitive sensor 2 as a reusable device and for using the enclosure 4 as a disposable device.

The object 3 is preferentially skin of a person or of an animal. The capacitive sensor apparatus 1 is preferentially adapted for capacitively sensing electrophysiological signals like ECG, EMG, EEG, EOG, EHG et cetera signals. The capacitive sensing apparatus 1 is preferentially adapted for sensing an electrophysio logical signal of a person or of an animal for monitoring the person or the animal.

The enclosure 4 comprises the contact side 6 and at least one lateral surrounding element 8 being, in this embodiment, a surrounding wall, for surrounding the capacitive sensor 2 for holding the capacitive sensor 2 in place.

At least the surface of the contact side 6 which is intended to contact the object 3 is preferentially made of a biocompatible material.

The enclosure 4 comprises a retaining element 7 for retaining the capacitive sensor 2 within the enclosure 4. The retaining element 7 is preferentially a notch element for clicking the capacitive sensor 2 into the enclosure 4 and for retaining the capacitive sensor 2 within the enclosure 4 in place. The retaining element 7 is preferentially adapted such that a "click" is heard and/or felt, if the capacitive sensor 2 is introduced into the enclosure 4 such that the capacitive sensor 2 is retained within the enclosure 4.

The surrounding element 8 is arranged at the contact side 6 and adapted to surround the capacitive sensor 2 for holding the capacitive sensor in place. The surrounding element 8 is flexible for forming a clamping mechanism for holding the capacitive sensor 2 in place.

The surrounding element 8 is a lateral element, i.e. a lateral wall for surrounding the capacitive sensor 2. The surrounding element 8 is adapted to conform to the shape of the capacitive sensor 2. In this embodiment, the capacitive sensor 2 has a cylindrical outer shape and the surrounding element 8 is a ring element. The surrounding element 8 is a single surrounding element which completely surrounds the capacitive sensor 2. However, instead of a single surrounding element, several surrounding elements can be used for surrounding the capacitive sensor.

Figure 2:
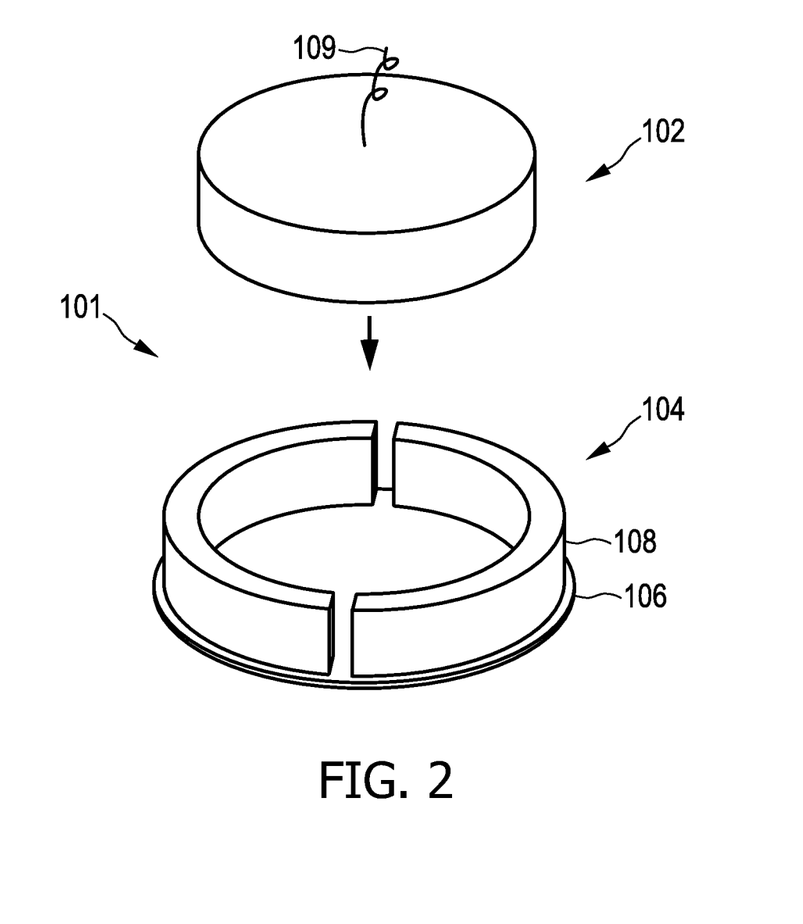

An enclosure 104 comprising a contact side 106 and two surrounding elements 108 is schematically and exemplarily shown in FIG. 2. These surrounding elements 108 are adapted to surround the cylindrically shaped capacitive sensor 102 with the wire 109. The two surrounding elements 108 form a ring element with two gaps which are located opposite to each other. Thus, the surrounding elements 108 form a segmented holder.

The capacitive sensor and the enclosure comprise preferentially a release mechanism for releasing the capacitive sensor from the enclosure. In the embodiments shown in the figures the surrounding elements are preferentially elastic allowing a person to push the surrounding elements of the enclosure for easily pressing the capacitive sensor out of the enclosure. In another embodiment, another release mechanism can be used, for example, at least one of the enclosure and of the capacitive sensor can comprises a spring forcing the capacitive sensor out of the enclosure.

Figure 3:
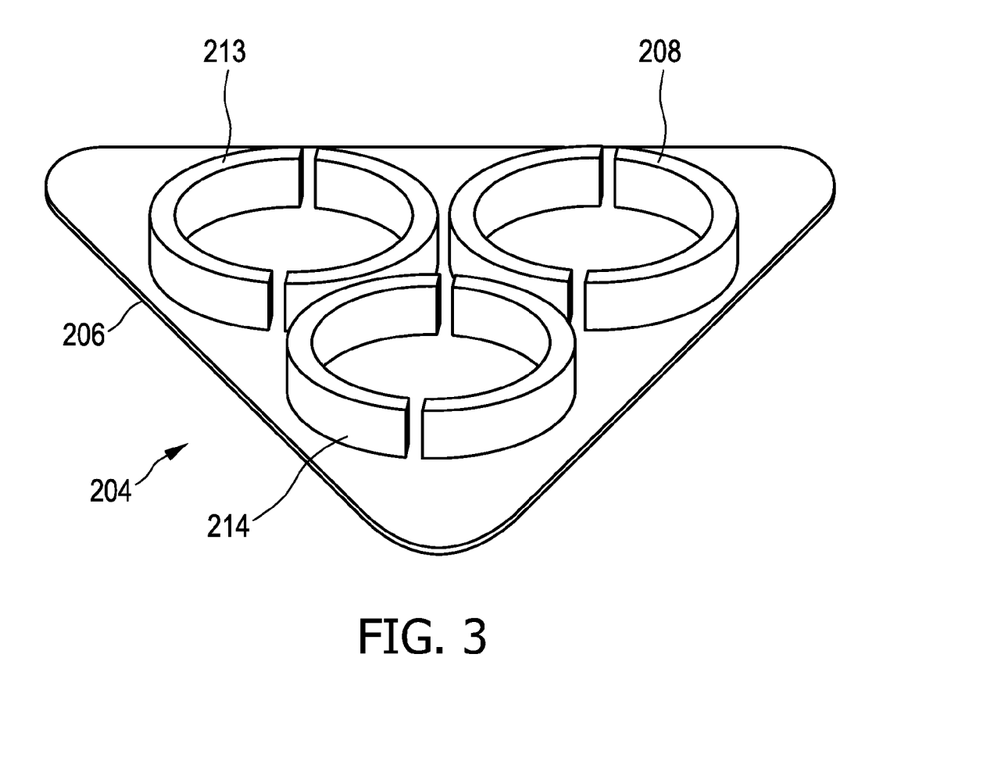

FIG. 3 shows schematically and exemplarily a further embodiment of the enclosure. The enclosure 204 shown in FIG. 3 is adapted for enclosing several capacitive sensors. The enclosure 204 comprises a contact side 206 on which three ring elements 208, 213, 214 formed by surrounding elements are provided. Each of these ring elements 208, 213, 214 comprises two gaps being located opposite to each other. In this embodiment, the contact side 206 has a substantially triangular shape with rounded corners. In another embodiment, the contact side 206 can have another shape, for example, a rectangular or a circular shape.

Thus, the enclosure 204 comprises a first at least one surrounding element, i.e. two first surrounding elements 208, for holding a first capacitive sensor in place, a second at least one surrounding element, i.e. two second surrounding elements 213, for holding a second capacitive sensor in place, and a third at least one surrounding element, i.e. two third surrounding elements 214, for holding a third capacitive sensor in place, wherein the first, second and third surrounding elements 208, 213, 214 are arranged on the same contact side 206.

This allows easily integrating several capacitive sensors on a single contact side. Moreover, this arrangement allows locating several capacitive sensors on the object by arranging only a single enclosure with the contact side on the object.

Figure 4:
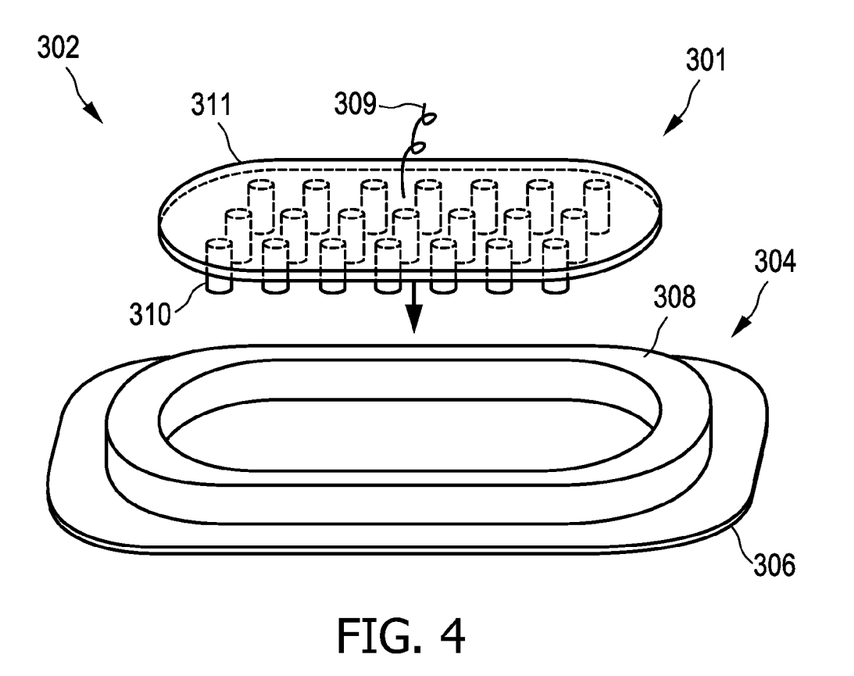

FIG. 4 shows schematically and exemplarily a further embodiment of a capacitive sensing apparatus.

The capacitive sensing apparatus 301 shown in FIG. 4 comprises a capacitive sensor 302 for capacitively sensing an object and an enclosure 304 for enclosing the capacitive sensor 302. The enclosure 304 comprises a contact side 306 for contacting the object during sensing. The enclosure 304 and the capacitive sensor 302 are adapted for sensing the object by the capacitive sensor 302 through the contact side 306 of the enclosure 304. Also the enclosure 304 and the capacitive sensor 302 are separable from each other for using the capacitive sensor 302 as a reusable device and for using the enclosure 304 as a disposable device.

The capacitive sensor 302 is formed of an array of capacitive sensing elements 310 arranged on a holding element 311. The capacitive sensing elements 310 generate a capacitive sensing signal which can be read out via the wire 309. The capacitive sensing elements 310 can be connected such and a control unit can be provided such that the capacitive sensing elements can be read out independently from each other or such that two or more, in particular, all capacitive sensing elements contribute to one capacitive sensing signal.

The use of such an array of capacitive sensing elements 310 allows to arrange several capacitive sensing elements 310 on the object by simply arranging the enclosure 304 on the object. Furthermore, this allows sensing the object at sensing positions which are close to each other.

The enclosure 304 of the capacitive sensing apparatus 301 comprises a surrounding element 308 adapted for surrounding the array of capacitive sensing elements 301. Also the surrounding element 308 can comprise gaps.

The described capacitive sensors and enclosures are preferentially coded, for example, by different colors, by different shapes or different icons. If several capacitive sensors and/or several enclosures are present, by using the coding it can be ensured that a capacitive sensor and an enclosure, which belong together, are put together.

The enclosures shown in the figures can comprises a cap (not shown in the figures) for closing the enclosure after the capacitive sensor has been introduced into the enclosure. In particular, the enclosure comprising the contact side and the at least one surrounding element form a container, wherein the cap can cover the remaining open side of the container. In an embodiment, the cap can be adapted such that the enclosure is automatically closed, if the capacitive sensor is introduced into the enclosure.

The contact side of the enclosure of the described embodiments can comprise an attachment means for holding the enclosure at a constant position on the object. The attachment means is preferentially an adhesive, in particular, a biocompatible adhesive, which is preferentially applied to the outer surface of the contact side of the enclosure. Such an attachment means is schematically and exemplarily shown in FIG. 6 which will be described further below. Instead of an adhesive another attachment means can be used, for example, a strapping element being adapted such that the enclosure can be hold on the object such that the contact side of the enclosure contacts the object while sensing the object capacitively.

The contact side of the described embodiments of the enclosure is preferentially a foil made of an insulating material. In other embodiments, the contact side can also be made of an electrically conducting material.

The contact side preferentially comprises, in particular, is made of, a high relative permittivity material. A high permittivity material is the material having a relative permittivity larger than 10, preferentially larger than 30, further preferred larger than 100 and even further preferred larger than 500.

A contact side comprising a high relative permittivity material ensures a sufficient capacitive coupling between the electrode, in particular, the capacitive sensor, and the object to be sensed. The contact side preferentially comprises at least one of the following materials: AgCl (11.2), BaO (34), BaTiO$_3$ (80-3600, anisotropic), BaZrO$_3$ (43), CaTiO$_3$ (165), Cd$_2$Nb$_3$O$_7$ (500-580), KH$_3$PO$_4$ (46), KNO$_3$ (25), KNbO$_3$ (700), KTaNbO$_3$ (6000-34000), NH$_4$HSO$_4$ (165), NaNbO$_3$ (670), Pb$_3$MgNb$_2$O$_4$ (10000), PbTiO$_3$ (200), SbSI (2000), SnTe (1770), SrTiO$_3$ (382), Ta$_2$O$_5$ (30-65, anisotropic), TiO$_2$ (86-170, anisotropic), WO$_3$ (300), ZrO$_2$ (12.5). In the previous list of materials the numbers in brackets denote the relative permittivity of the respective material.

The contact side, in particular, the surface of the contact side facing the object during sensing, is preferentially non-toxic, in particular, is preferentially biocompatible. Thus, the contact side comprises preferentially at least one of the following materials: AgCl, BaO, BaTiO$_3$, BaZrO$_3$, CaTiO$_3$, KH$_3$PO$_4$, Ta$_2$O$_5$, TiO$_2$, WO$_3$ and ZrO$_2$. These materials are preferentially used as a solid insulating coating on the contact side of the enclosure.

If the contact side comprises, in particular, is made of, a high relative permittivity material, the capacitive sensor and the enclosure are preferentially adapted such there is no air gap between the capacitive sensor and the enclosure towards the contact side.

In another embodiment, the contact side of the enclosure can comprise, in particular, can be made of, a low relative permittivity material.

A low permittivity material is a material having a relative permittivity smaller than 10, preferentially smaller than 5 and further preferred smaller than 3.

If the appearance of air gaps is likely, a relative permittivity material as close as possible to air reduces motion artifacts. Therefore, also following materials can be preferred materials for the contact side: non-oxygen containing polymers like polytetrafluorethylene (2.1), polyethylene/polypropylene (2.3), polybutadiene (2.5), polystyrene (2.6), natural rubber (2.6), polycarbonate (2.9). Also silicon rubber (3) is a preferred material of the contact side, in particular, because of its good biocompatible nature. Also in this paragraph the numbers in brackets denote relative permittivity values.

Also nanostructured materials having a relative permittivity smaller than 2.0, further preferred smaller than 1.5, and even further preferred smaller than 1.2 can be used as material for the contact side. These materials can be useful to create a well controlled thickness with a low relative permittivity while maintaining a barrier between the re-useable capacitive sensor and the object, in particular, the skin, for hygienic purposes.

The low relative permittivity material is preferentially used if air gaps are likely, because a relative permittivity as close as possible to air reduces motion artifacts caused by relative motions between the surface of the object and the electrode of the capacitive sensing apparatus.

Referring again to FIG. 1, the capacitive sensor 2 comprises an electrode 12, electronics 14 for reducing the impedance of the capacitive sensor and an electrical shielding 13 for shielding the electronics 14 and the electrode 12, wherein the electronics 14 are located within the electrical shielding 13.

The electrode 12, the electrical shielding 13 and the electronics 14 are formed as a single component which can be arranged within the enclosure 4. The electrode 12 is an electrode plate. Since the capacitive sensor 2 comprises the electrode 12, the electronics 14 and the electrical shielding 13, the capacitive sensing apparatus 1 can easily be put together by introducing the capacitive sensor 2 in the enclosure 4. The generated capacitive sensing signals can be read out via the wire 9. The capacitive sensor 2 can also comprise more modules for further functions, for example, the capacitive sensor 2 can comprise a wireless communication unit instead of using the wire 9, a battery, a signal processing unit et cetera. The shielding 13 can be a passive shielding or an active shielding.

The capacitive sensor 2 further comprises a casing 15 being made of an insulating material and/or of a conducting material.

Figure 5:
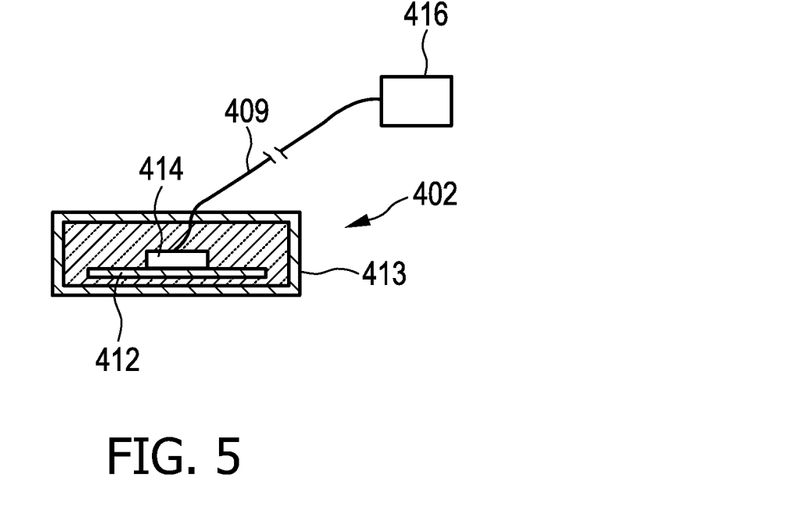
FIG. 5 shows schematically and exemplarily an embodiment of a capacitive sensor of a capacitive sensing apparatus.

FIG. 5 shows schematically and exemplarily a further embodiment of a capacitive sensor. The capacitor sensor 402 shown in FIG. 5 comprises an electrical shielding 413 formed as a casing made of conducting material like copper. A side of the casing, which is intended to face the object while sensing, forms the electrode 412. The electronics 414 and the electrode 412 are arranged within the casing, wherein, if the casing 413 is made of a conducting material, the electrode 412 is not in electrical contact with the casing 413. Therefore, if the casing 413 is made of a conducting material, an insulating material is provided at least between the electrode 412 and the casing 413, i.e. below the electrode 412 and the casing 413. The sensing signal generated by the capacitive sensor can be read out via the electrical connection 409 being, in particular, a wire. The generated sensing signal is transferred to a control and output unit 416 for controlling the capacitive sensor and for outputting the generated sensing signal. The control and output unit 416 can also comprise a signal processing unit for processing the sensing signal like filtering the signal before outputting the same. Also the capacitive sensors shown in the other figures can be connected to a control and output unit for controlling the capacitive sensor and for outputting a sensing signal generated by the capacitive sensor. The casing formed by the electrical shielding 413 is formed such that it corresponds to the shape of the enclosure, in which the capacitive sensor is intended to be introduced. Preferentially, the casing has a cylindrical shape. However, the casing can also have another shape, for example, a rectangular shape.

Figure 6:
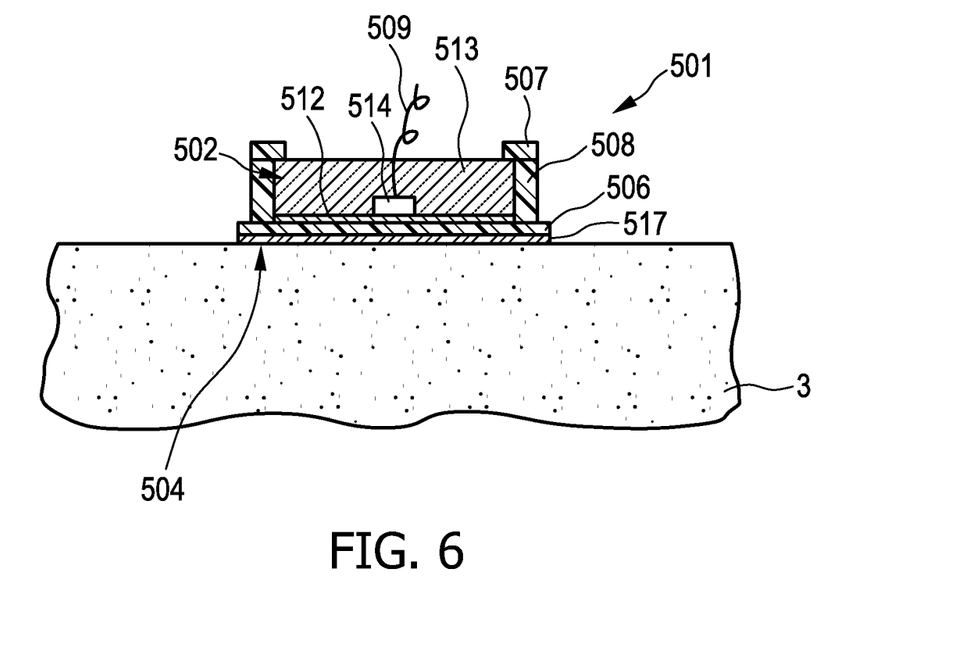
FIG. 6 shows a further embodiment of a capacitive sensing apparatus and FIG. 7 shows exemplarily a flow chart illustrating a capacitive sensing method.

FIG. 6 shows schematically and exemplarily a further embodiment of a capacitive sensing apparatus. The capacitive sensing apparatus 501 shown in FIG. 6 comprises a capacitive sensor 502 for capacitively sensing the object 3 and an enclosure 504 for enclosing the capacitive sensor 502. The enclosure 504 comprises a contact side 506 for contacting the object 3 during sensing. An adhesive is applied on the surface of the contact side 506 facing the object 3 during sensing, i.e. an adhesive is applied on the outer surface of the contact side 506. The adhesive forms a layer 517 being an attachment means for holding the enclosure 504 at a constant position on the object 3.

The enclosure 504 comprises an electrode 512 and the capacitive sensor 502 comprises electronics 514 for reducing the impedance of the capacitive sensor and an electrical shielding 513 for shielding the electronics 514 and the electrode 512. The enclosure 504 and the capacitive sensor 502 are adapted such that the electrode 512 and the electronics 514 are electrically connected, if the capacitive sensor 502 is arranged within the enclosure 504. Thus, the capacitive sensor 502 comprises contacts for contacting the electronics 514 with the electrode 512 located in the enclosure 504.

Although in the above described embodiments which are shown in the figures the wiring is arranged in the capacitive sensor which can be electrically connected to a control and output unit, it is also possible that the wiring is arranged in the enclosure, wherein the enclosure comprises an electrical contact and wherein the capacitive sensor comprises a corresponding electrical contact such that the capacitive sensor is electrically connected to the enclosure such that the capacitive sensor is electrically operable. For example, the generated capacitive signal can be transferred to an external control and output unit via the wiring arranged in the enclosure.

The whole or only a part of the wiring can be wired through the enclosure, for example, for establishing a common reference (ground) between multiple capacitive sensors.

Figure 7:
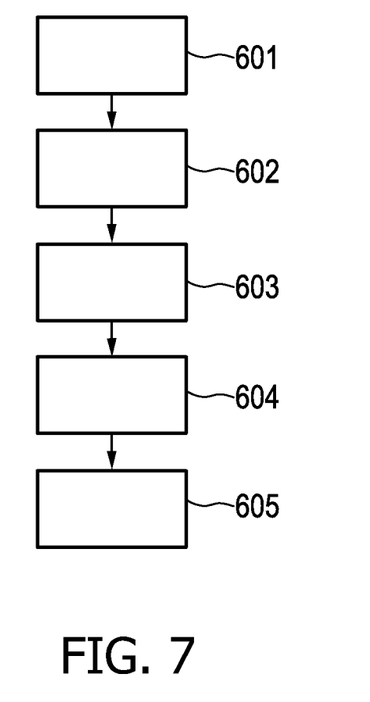

In the following an embodiment of a capacitive sensing method will exemplarily described with reference to a flow chart shown in FIG. 7.

In step 601, the capacitive sensor is separable enclosed within the enclosure.

In step 602, the enclosure comprising the capacitive sensor is attached to an object, in particular, attached to the skin of a person or of an animal, and in step 603 the object, in particular, the skin of a person or of an animal, is sensed through the contact side of the enclosure by the capacitive sensor. Preferentially, in step 603 electrophysiological signals of a person or of an animal are measured.

After the measurement is completed, in step 604 the enclosure comprising the capacitive sensor is detached from the object, and in step 605 the capacitive sensor is separated from the enclosure for using the capacitive sensor as a reusable device and for using the enclosure as a disposable device.

Capacitive electrophysiological sensors are attractive because of their inherent comfort. Since no conducting, in particular, galvanic, contact is needed between skin and electrode, a wet gel contact or skin preparation is no longer needed.

The capacitive coupling between the sensor and the skin can be considered as a parallel capacitor. The capacitance C for a parallel plate capacitor is given by: $C=\epsilon_0 \epsilon_{rel} A/d$ in which $\epsilon_0$ is the permittivity of vacuum ($8.85 \times 10^{-12}$ F/m), $\epsilon_{rel}$ the relative permittivity, A is the sensor area (typically 0.5-4 cm$^2$) and d is the distance between the 'plates' (body and electrode). The volume created by the sensor area A and the distance d can be filled with an insulating material.

The capacitive sensing apparatus comprising the capacitive sensor and the enclosure can be used in the fields of personal health, mobile monitoring, life style et cetera. However, the capacitive sensing apparatus can also be used in more traditional fields of electrophysiological sensing, for example, in regular patient ECG monitoring in a hospital. In a hospital a capacitive sensing apparatus has to be clean when used on a different patient. This is achieved in accordance with the invention by providing a disposable enclosure, in which a reusable capacitive sensor can be introduced. The attachment means of the enclosure can be used for accurately positioning the capacitive sensing apparatus on a body of a person or of an animal for measuring electrophysiological signals.

The capacitive sensing apparatus comprising the capacitive sensor and the enclosure have the advantage, in comparison to the use of traditional electrodes for measuring electrophysiological signals, that it is not needed to use a conductive gel that dries out over time and also skin preparation for better electrical contact is not required. Since a conductive gel is not needed by the capacitive sensing apparatus, skin irritations caused by the conductive gel can be prevented. Furthermore, measuring of electrophysiological signals through other objects like bandages becomes possible because of the capacitive sensing in the field in which generally contact electrodes are used for sensing electrophysiological signals.

Although in the above described embodiments surrounding elements are described, wherein, in particular, two flexible parts form a ring with two oppositely located gaps for holding the capacitive sensor in place, any other (segmented or non-segmented) design of the enclosure could be used that keeps the sensor in place.

Although in the above described embodiments the capacitive sensor has preferentially a cylindrical shape, the capacitive sensor can also have another shape like a rectangular shape. The enclosure is than adapted to conform to the respective shape of the capacitive sensor.

Although in the above described embodiments a certain number of capacitive sensors can be enclosed by a single enclosure, the enclosure can also be adapted to enclose another number of capacitive sensors, for example, the enclosure can be adapted to enclose one, two, three or more capacitive sensors.

Although in the above described embodiments the contact side comprises, in particular, is made of, an insulating material, the contact side can also comprise, in particular, can also be made of, a conducting material.

The adhesive is preferentially an adhesive ensuring a good fixation to the skin of the body of a person or of an animal. However, the adhesive can also be an adhesive that is suitable to adhere to other materials, for example, textile, when an application is targeted in which the capacitive sensor measures through someone's clothes or through bandages. The enclosure can also be adapted such that it connects to the hair of the skull, if a person or an animal is sensed. Instead of or in addition to using a high relative permittivity material for the contact side of the enclosure, the capacitive sensor can be coated with a high relative permittivity material. Thus, the high relative permittivity material can be applied as a solid insulating coating on the capacitive sensor.

The capacitive sensing apparatus is preferentially adapted to be used for probing electrophysiological fields (ECG, EMG, EEG, EOG, EHG, . . . ). Some examples where the capacitive sensing apparatus can be used are patient monitors (mostly ECG), EEG probing device (clinical), Brain Computer Interface (BCI), pregnancy belts containing sensors for monitoring baby condition or uterine activity, EMG probing device to monitor muscle use in order to prevent muscle overload or RSI, device that monitors ECG or EMG during physical activity/sports or devices that interpret emotions based on electrophysiological signals. Since capacitive sensors have the unique capability to measure through insulating materials new possibilities arise like measuring through bandages, for example, in case of burn wounds or measure electrophysiological signals in a 'smart bed'.

Although in the above described embodiments, an application of the capacitive sensing apparatus in a hospital is exemplarily mentioned, the capacitive sensing apparatus can also be used in another environment, for example, in the field of home monitoring for user friendly probing of body vital signals like ECG.

Although in the above described embodiments, different enclosures and capacitive sensors have been described, the features of these enclosures and these capacitive sensors can be combined, for example, the embodiments shown FIGS. 3 and 4 can be combined such that each of the ring elements 208, 213 and 214 can enclose an array of capacitive sensing elements.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or devices may fulfill the functions of several items recited in the claims. The mere fact that certain measures are recited in mutually different dependent claims does not indicate that a combination of these measures cannot be used to advantage.

The invention claimed is:

1. A capacitive sensing apparatus for capacitively sensing electrophysiological signals in a person or animal, comprising:
   a capacitive sensor for capacitively sensing the electrophysiological signals generated by the person or animal; and
   an enclosure for enclosing the capacitive sensor, wherein the enclosure has a contact side configured to contact the person or animal during sensing to capacitively sense the electrophysiological signals through the contact side of the enclosure; and
   wherein the enclosure and the capacitive sensor are separable from each other such that the capacitive sensor is a reusable device and the enclosure is a disposable device, and
   wherein the enclosure comprises at least one surrounding element, which peripherally surrounds the capacitive sensor and releasably engages the contact side, the surrounding element being flexible so as to click the capacitive sensor into place and selectively release the capacitive sensor.

2. The capacitive sensing apparatus as claimed in claim 1, wherein the enclosure is configured to retain several capacitive sensors in a preselected relationship.

3. The capacitive sensing apparatus as claimed in claim 2, wherein the enclosure comprises a first surrounding element for holding a first capacitive sensor in place and at least one additional surrounding element for holding at least one additional capacitive sensor in place, wherein the first surrounding element and the at least one additional surrounding element are arranged on the same contact side.

4. The capacitive sensing apparatus as claimed in claim 1, wherein the capacitive sensor is mounted in the enclosure such that there is no air gap between the capacitive sensor and the enclosure towards the contact side.

5. A capacitive sensing apparatus for capacitively sensing electrophysiological signals in a person or animal, comprising:
   a capacitive sensor for capacitively sensing the electrophysiological signals generated by the person or animal; and
   an enclosure for enclosing the capacitive sensor, wherein the enclosure has a contact side configured to capacitively couple with the person or animal without a wet gel contact or skin preparation during sensing to capacitively sense the electrophysiological sings that the contact side of the enclosure,
   wherein the enclosure and the capacitive sensor are separable from each other such that the capacitive sensor is a reusable device and the enclosure is a disposable device, and
   wherein the contact side comprises a high relative permittivity material with a permittivity greater than 10.

6. The apparatus as claimed in claim 5, further comprising a spring release mechanism including a spring urges the capacitive sensor out of the enclosure.

7. The apparatus as claimed in claim 5, wherein the enclosure includes an elastic surrounding element which holds the capacitive sensor in place and can be pushed for detaching the capacitive sensor from the enclosure.

8. The capacitive sensing apparatus as claimed in claim 5, wherein the enclosure is configured to retain several capacitive sensors in a preselected relationship.

9. The capacitive sensing apparatus as claimed in claim 8, wherein the capacitive sensor includes an array of capacitive sensing elements mounted in the enclosure.

10. The capacitive sensing apparatus as claimed in claim 9, wherein the enclosure comprises at least one surrounding element for surrounding the array of capacitive sensing elements.

11. A capacitive sensing apparatus for capacitively sensing an object, comprising:
    a capacitive sensor for capacitively sensing an electrophysiological signal of a person or animal;
    an enclosure for enclosing the capacitive sensor,
        wherein the enclosure is adapted for sensing the electrophysiological signal of the person or animal by the capacitive sensor and wherein the enclosure is separable from the capacitive sensor for using the enclosure as a disposable device,
        wherein the enclosure comprises at least one surrounding element, which is arranged on the contact side and which is adapted to surround the capacitive sensor for holding the capacitive sensor in place,
        wherein the at least one surrounding element is flexible for forming a clamping mechanism for holding the capacitive sensor in place and is configured to flex and release the capacitive sensor in response to pushing on the enclosure.

12. The capacitive sensing apparatus as claimed in claim 11, wherein the capacitive sensor comprises:
    an electrode;
    electronics configured to reduce the impedance of the capacitive sensor; and
    an electrical shield for shielding the electronics and the electrode,
    wherein the electrode, electronics, and shielding are formed as a single component which is configured to be releasably engaged within the enclosure.

13. The capacitive sensing apparatus as claimed in claim 12, wherein the electrical shielding includes one of active shielding or passive shielding.

14. The capacitive sensing apparatus as claimed in claim 11, wherein the capacitive sensor includes an array of capacitive sensing elements arranged on a holding element and the capacitive sensing elements being configured to be read out independently or in combinations such that two or more capacitive sensing elements contribute to one capacitive sensing signal.

15. The capacitive sensing apparatus as claimed in claim 11, wherein at least one of the capacitive sensor and the enclosure includes a notch retaining element which clicks the capacitive sensor into the enclosure.

16. A capacitive sensing method for sensing electrophysiological signals generated by a person or animal, comprising:
    enclosing a capacitive sensor in an enclosure which includes at least one elastic surrounding element, which peripherally surrounds and releasably engages the capacitive sensor and a contact side for contacting the person or animal during sensing, the surrounding element being flexible and configured to click the capacitive sensor into place and selectively release the capacitive sensor;
    wherein the enclosing step includes pressing the capacitive senor into the enclosure until the capacitive sensor clicks into place providing feedback assuring that the capacitive sensor is in place
    mounting the contact side of the enclosure on the person or animal without wet gel or skin preparation; and capacitively sensing the electrophysiological signals generated by the person or animal through the contact side of the enclosure with the capacitive sensor.

17. The capacitive sensing method as claimed in claim 16, after sensing the electrophysiological signals generated by the person or animal, removing the capacitive sensor from the enclosure; discarding the enclosure; and enclosing the capacitive sensor in another for use on another person or animal.

* * * * *